(12) United States Patent
Thorsgard

(10) Patent No.: US 7,727,234 B2
(45) Date of Patent: Jun. 1, 2010

(54) APPARATUS AND METHOD FOR ANTERIOR CRUCIATE REPAIR

(76) Inventor: Eric O. Thorsgard, 3015 Madison Ave., SW., Bemidji, MN (US) 56601

( * ) Notice: Subject to any disclaimer, the term of this patent is extended or adjusted under 35 U.S.C. 154(b) by 673 days.

(21) Appl. No.: 11/182,698

(22) Filed: Jul. 15, 2005

(65) Prior Publication Data

US 2006/0025776 A1 Feb. 2, 2006

Related U.S. Application Data

(60) Provisional application No. 60/588,499, filed on Jul. 15, 2004.

(51) Int. Cl.
*A61B 17/14* (2006.01)
(52) U.S. Cl. ........................................ 606/82
(58) Field of Classification Search ............ 606/79, 606/84, 86–88, 96
See application file for complete search history.

(56) References Cited

U.S. PATENT DOCUMENTS

| | | | | |
|---|---|---|---|---|
| 4,627,425 A | * | 12/1986 | Reese | 606/87 |
| 4,703,751 A | * | 11/1987 | Pohl | 606/62 |
| 4,952,213 A | * | 8/1990 | Bowman et al. | 606/79 |
| 4,955,888 A | * | 9/1990 | Slocum | 606/82 |
| 5,053,037 A | * | 10/1991 | Lackey | 606/79 |
| 5,053,039 A | * | 10/1991 | Hofmann et al. | 606/87 |
| 5,147,364 A | * | 9/1992 | Comparetto | 606/85 |
| 5,234,433 A | * | 8/1993 | Bert et al. | 606/88 |
| 5,578,038 A | | 11/1996 | Slocum | |
| 5,601,565 A | * | 2/1997 | Huebner | 606/87 |
| 2002/0122703 A1 | * | 9/2002 | Czyzewski et al. | 408/1 R |

\* cited by examiner

*Primary Examiner*—Eduardo C Robert
*Assistant Examiner*—Elana B Fisher
(74) *Attorney, Agent, or Firm*—Moore & Hansen, PLLP

(57) ABSTRACT

A system and method for repairing anterior cruciate injuries in animals is disclosed. The system includes a fixture used to locate a pilot hole in a tibia, a drill guide used to locate and drill additional holes in the tibia, an angle gauge used to position the drill guide so that it is able to locate and drill additional holes in the tibia, a saw assembly that separates the proximal end of the tibia from the shaft of the tibia. The repositioned proximal end may be secured to the tibia by an optional fixation plate or by a suitable adhesive.

18 Claims, 8 Drawing Sheets

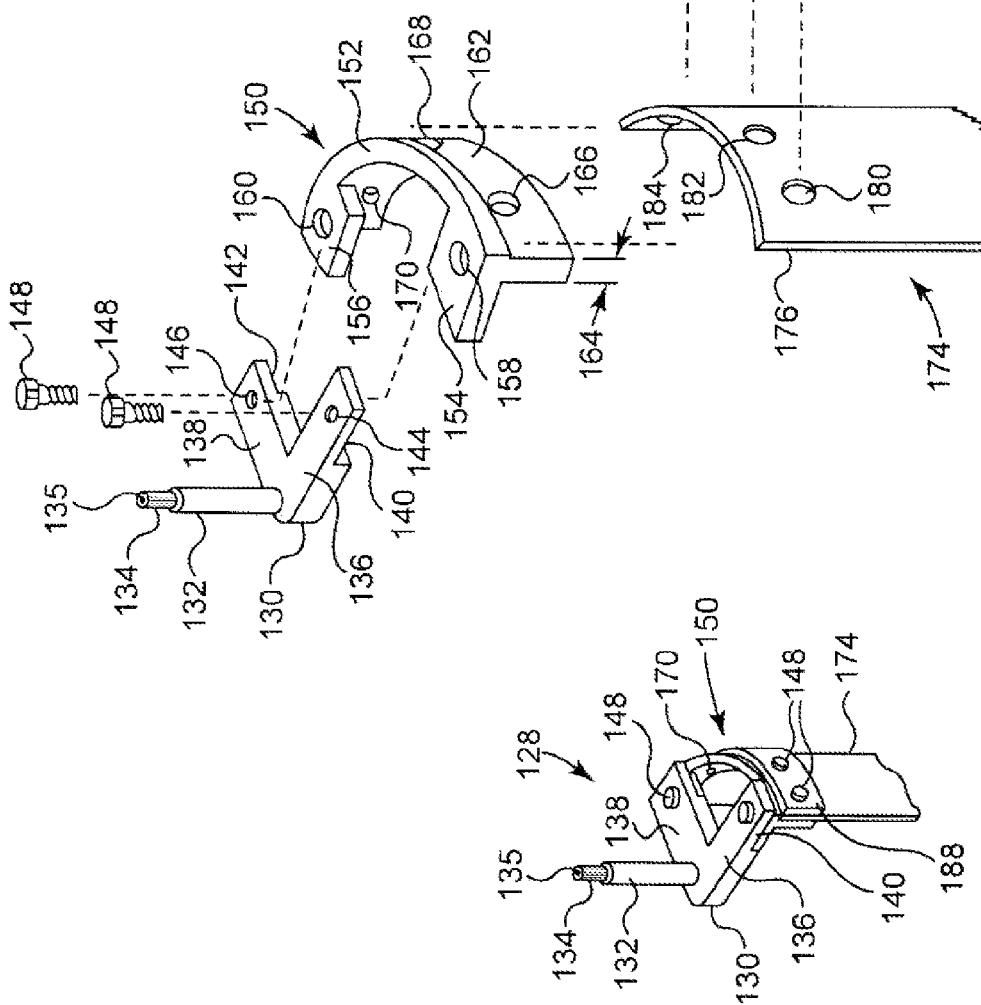

US 7,727,234 B2

APPARATUS AND METHOD FOR ANTERIOR CRUCIATE REPAIR

This application claims the benefit of prior filed, co-pending provisional application Ser. No. 60/588,499 filed Jul. 15, 2004.

FIELD OF THE INVENTION

This disclosure relates to veterinary medicine. More specifically, this disclosure relates to an apparatus and method for repairing anterior cruciate ligaments in animals.

BACKGROUND OF THE INVENTION

Anterior cruciate ligament repair for animals such as dogs have been known and practiced for a number of years. There are several methods of repair, one of which is "tibial plateau leveling osteotomy". In this procedure, the upper portion of the tibia is separated from the upper portion of the tibia, repositioned, and then secured relative to the tibia. In repositioning the tibial plateau, slack in the anterior cruciate can be taken up and the joint can be strengthen and reinforced. See, for example U.S. Pat. No. 4,677,793.

A drawback with existing procedures it is difficult to make saw cuts that are perpendicular to the weight-bearing axis of tibia.

Another drawback with existing procedures is that it is difficult to accurately reposition the proximal end of the tibia after it has been sawn from the shaft of the tibia.

Another drawback with existing systems is that they are not designed to be used with differently sized animals.

Yet another drawback with existing systems is that securement of the repositioned proximal end of the tibia is difficult and often inadequate.

SUMMARY OF THE INVENTION

A system and method for repairing anterior cruciate injuries in animals is disclosed. The system comprises a fixture used to locate a pilot hole in a tibia, a drill guide used to locate and drill additional holes in the tibia, an angle gauge used to position the drill guide so that it is able to locate and drill additional holes in the tibia, a saw assembly that separates the proximal end of the tibia from the shaft of the tibia, and the option of using either a fixation plate or bone cement to secure the proximal end of the tibia to the shaft of the tibia.

The fixture is used to locate and drill a pilot or first transverse hole in the proximal end of the tibia. The fixture includes a frame and an arm that is pivotally attached thereto. The frame includes an aperture that is configured to slidingly receive a guide pin that is temporarily inserted into the medullary cavity of the tibia. The arm includes an aperture that is perpendicular to the aperture of the frame, and which is configured and arranged to guide a drill that forms a pilot hole in the tibia.

The drill guide, which is bi-directional or reversible, and which is removably attached to the tibia so that it may rotate about the axis of the pilot hole, is used to locate and drill additional holes in the tibia. The drill guide and has opposing ends and a plurality of generally parallel apertures that are spaced at predetermined distances therefrom in a staggered relation. This allows the guide to locate and guide drills so that they are able to form holes in a predetermined pattern.

The drill guide is also used in conjunction with an angle gauge, which orients the drill guide with respect to the tibia. This enables the drill guide to locate additional drilling locations of the pattern of holes that are offset with respect to the longitudinal axis of the tibia.

The saw assembly includes a cannulated mandrel, an adaptor, a saw blade, and a collar. The mandrel is configured to removably retain an adaptor, which has a downwardly extending skirt located a predetermined distance from the cannulation axis of the mandrel. The skirt has inner and an outer surface, each of which may have a saw blade positioned and retained thereagainst by a collar. The saw assembly may include additional adaptors having skirts that are located at other predetermined distances from the cannulation axis of the mandrel, so that other saw blades may be used in the saw assembly.

The optional fixation plate used to orient and connect the proximal end of the sawn tibia to the shaft of the tibia includes a plurality of pre-drilled apertures that are arranged in a predetermined pattern and which can find correspondence to the apertures in the drill guide.

Alternatively, the proximal end of the sawn tibia may be connected to the shaft of the tibia by adhesive material, preferably bone cement.

Additional advantages and features of the invention are set forth in part in the description which follows, and in part will become apparent to those skilled in the art upon examination of the following or may be learned by practice of the invention. The features and advantages of the invention may be realized and attained by means of the instrumentalities and combination particularly pointed out in the appended claims.

DESCRIPTION OF THE DRAWINGS

FIG. 9b is a side plan view of the angle gauge of FIG. 9a;

FIG. 10 is a perspective view of a preferred embodiment of a saw assembly of the tibial plateau leveling osteotomy system;

FIG. 11 is a perspective, exploded view of the saw assembly of FIG. 10;

FIG. 12 is a perspective view of an interchangeable component of the saw assembly of FIGS. 10 and 11;

DETAILED DESCRIPTION

Figure 1:
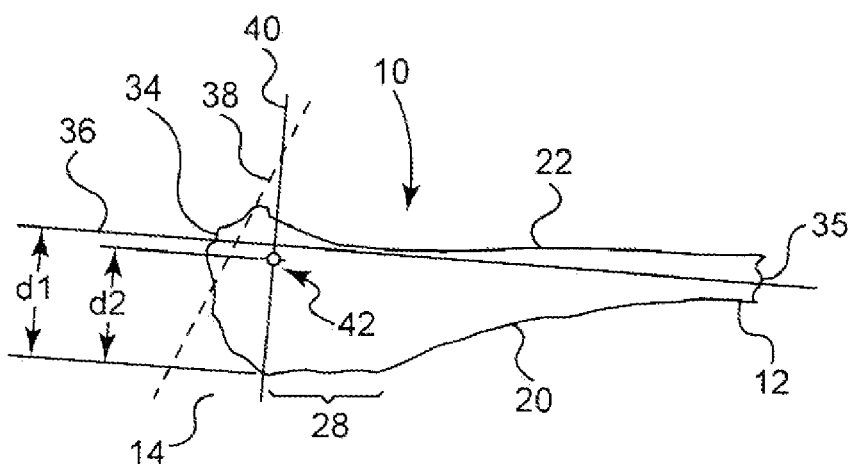
FIG. 1 is a partial, lateral side view of the upper or proximal end of a tibia.

Before the actual osteotomy begins, the location of a transverse pilot hole is determined. This is accomplished by taking a lateral radiograph of the tibia to be operated on. Using the radiograph image, which shows a tibia 10 having distal 12 and proximal 14 ends as well as posterior 22 and anterior 20 surfaces, the inter tubercle eminence 34 is located and a line 36 is drawn along the length of the tibia 10 to the middle 35 of the distal end 12 of tibia 10. The ensuing line 36 represents the weight bearing axis of the tibia 10. Next, the tibial plateau, represented by dashed line 38, is located and drawn. Then, a line 40 is drawn from the uppermost or proximal extend of the tibial crest 28 located on the anterior surface 20 of the tibia 10 so that it intersects the weight bearing axis 36 at a substantially perpendicular angle. The pilot hole, which extends transversely between the sides of the tibia, will be located along line 40. To determine the location of the pilot hole, the distance d1 along line 40 between the tibial crest 28 and the weight bearing axis 36 is measured. Then, the distance d1 is multiplied by a factor of about 0.7 to produce the value d2, which is then measured along line 40 starting from the anterior surface 20 and terminating at center point 42. The terminus or center point 42, which is determined by distance d2 locates the position of a pilot hole 70, which will be discussed later in detail.

Figure 2:
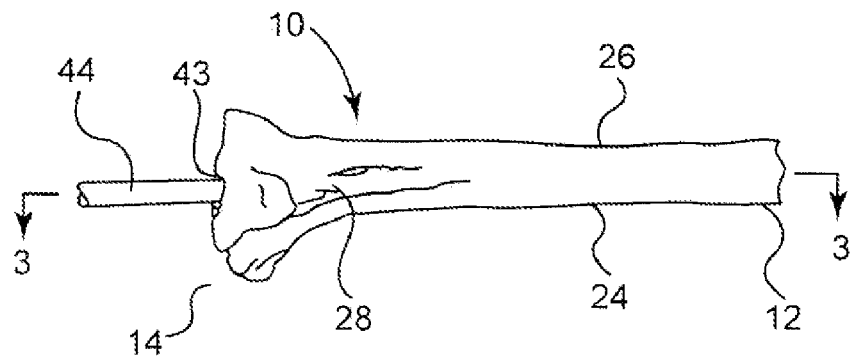
FIG. 2 is a partial, anterior view of the tibia of FIG. 1.
Figure 3:
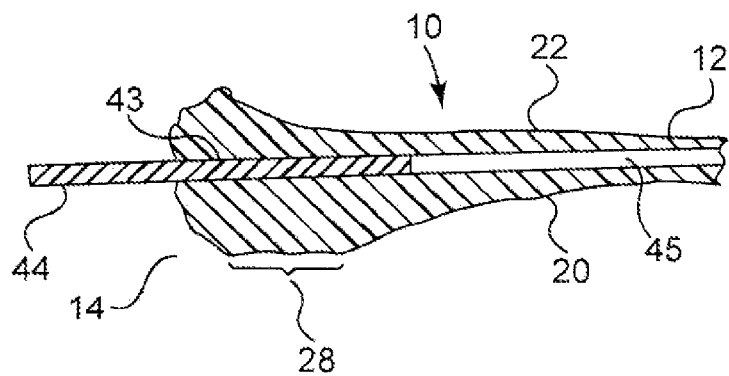
FIG. 3 is a is a partial, sectional, lateral side view of the tibia of FIG. 1.
Figure 4:
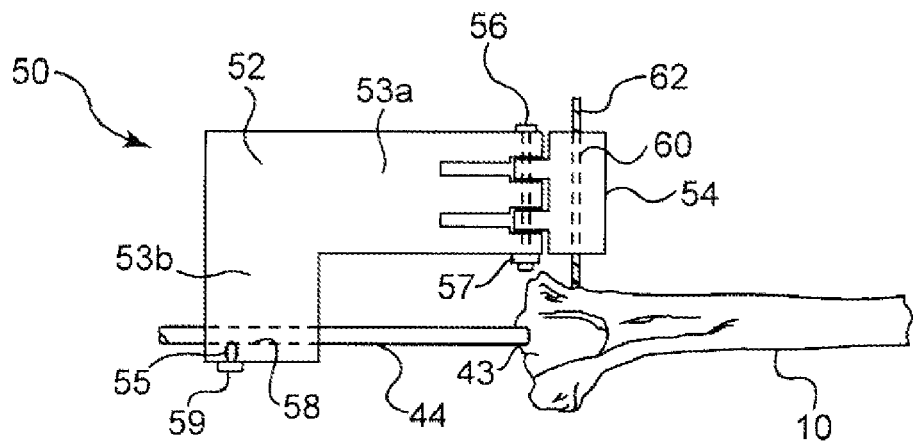
FIG. 4 is a plan view of a preferred embodiment of a fixture as used to drill a pilot hole in the proximal end of the tibia of FIG. 2.

To assist in drilling the pilot hole 70, a fixture is used (see 50 in FIG. 4). However, before the pilot hole 70 can be drilled, the fixture 50 has to be temporarily attached to the tibia 10. Preferably, this is achieved by using a guide pin 44, which is temporarily inserted into a pre-drilled hole 43 that is located at the proximal end 14 of the tibia 10 and which is in substantial alignment with the medullary cavity 45 of the tibia. As will be understood, the guide pin 44 will be of sufficient size to be frictionally retaining by the tibia 10 as it resides in hole 43 and cavity 45 (see FIG. 3). As depicted in FIGS. 2 and 3, the guide pin 44, which extend partially into the medullary cavity 45, is centrally located with respect to the anterior 20, posterior 22, lateral 24, and medial 26 surfaces of the tibia 10.

Figure 5:
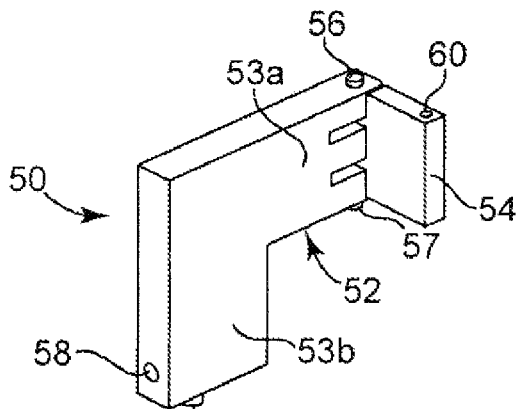
FIG. 5 is a perspective view of the fixture of FIG. 4.

A preferred embodiment of a fixture 50 used to drill a pilot hole is shown in FIGS. 4 and 5. As can be seen, fixture 50 comprises a generally L-shaped frame 52 having segments 53a, 53b, and an arm 54 that is operatively connected thereto by pin 56. Frame segment 53b includes an aperture 58 that is sized to slidably receive guide pin 44 so that the fixture 50 may be operatively connected to the tibia 10 and movable towards and away from the proximate end 14 in a controlled manner. In order to prevent unintentional or accidental movement between the frame 52 and the guide pin 44, frame segment 53b may include a threaded aperture 55 that intersects aperture 58, and a securement member 59 such as a set screw that is received in the threaded aperture 55. Operation of the securement member 59 is self evident and will not be further discussed. As will be noted, the pin 56 connection between arm 54 and frame segment 53a allows the arm 54 to be rotated with respect to the frame 52 and allows an aperture 60 in arm 54 to be positioned above center point 42. Note that the rotational axes of apertures 58 and 60 are substantially orthogonal to each other and that the orthogonal relation between apertures 58 and 60 is maintained as the arm 54 moves relative to the frame 52. After the aperture 60 is positioned over the center point 42, a drill 62 is used to form pilot hole 70 (see FIG. 6). The connection between frame section 53a and arm 54 will now be briefly discussed. In general, frame section 53a and arm 54 are provided with barrels or knuckles that have axial bores, and which are arranged in an alternating manner to form a hinge structure that is held together by pin 56. The barrels of frame section 53a are separated from each other by deep kerfs, which permit a measure of resiliency therebetween. As will be appreciated pin 56 may be provided with a threaded end and a fastening element 57, which may be tightened so that the outer barrels of frame section 53a may be brought towards each other so that they are able to frictionally contact the barrels of arm 54. Thus, the arm 54 may be adjusted to a secured in particular orientation relative to the frame 52, if desired.

Once the pilot hole 70 has been drilled, the fixture 50 is removed from the tibia 10 by removing the guide pin 44 and sliding the fixture 50 off of the drill 62 used to form the pilot hole. Alternatively, the fixture 50 may be removed by removing the drill 62 from pilot hole 70, sliding the fixture 50 off the guide pin 44, removing the guide pin 44, and replacing the drill 62 back into the pilot hole 70 in the tibia 10.

Figure 6:
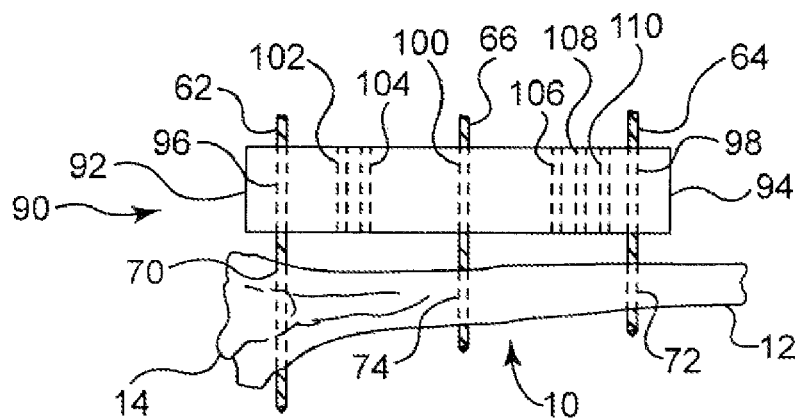
FIG. 6 is a plan view of an embodiment of guide used to locate and drill secondary holes in the tibia of FIG. 2.
Figure 7:
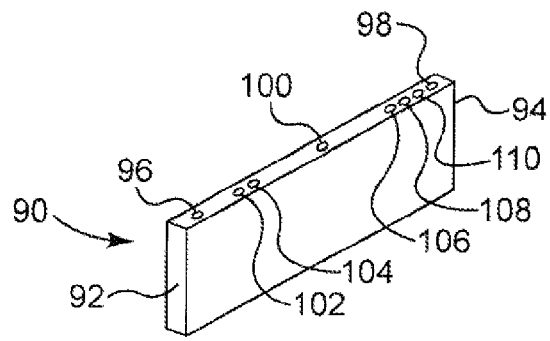
FIG. 7 is a perspective view of the guide of FIG. 6.
Figure 8:
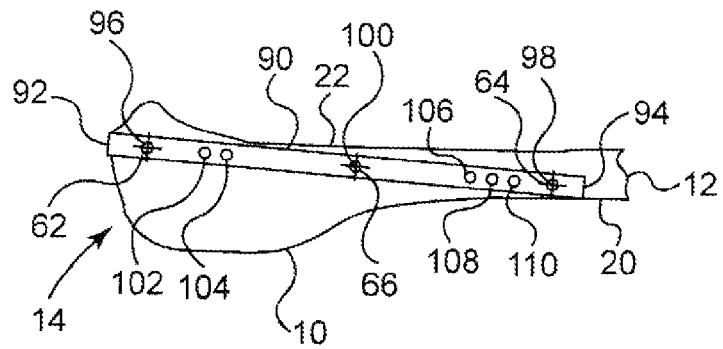
FIG. 8 is a plan view of the guide of FIGS. 6 and 7 as it is used to locate and drill holes in the tibia of FIG. 6.

Additional holes are then located and drilled in the tibia 10 using a bi-directional guide 90. As depicted in FIGS. 6-8, the bi-directional drill guide 90 is generally rectangular in shape and includes a first end 92, a second end 94, and a plurality of generally parallel apertures 96, 98, 100, 102, 104, 106, 108, and 110 that extend transversely through the guide 90, and which are configured and arranged to receive drill bits. Preferably, the end apertures 96 and 98 are equal distance from the middle aperture 100.

The additional holes may be located and drilled in the tibia 10, as follows. With drill 62 extending from the pilot hole 70 in the tibia, the guide 90 is slid onto the drill 62 at end aperture 96. Then, the guide 90 is rotated about the drill 62 to a point where the end aperture 98 is in close proximity to the anterior surface 20 of the tibia, as shown in FIG. 8. A second hole 72 is then drilled using drill 64 and aperture 98. The drill 64 is left in the aperture 98 and the second hole 72, and a third hole 74 is drilled using drill 66 and aperture 100.

A fourth hole 76 may then be then located and drilled in the proximal end 14 of the tibia 10. However, before the fourth hole is drilled, it is advisable to check to verify, that the location and size that of the cut that will be made during the osteotomy procedure. This can be achieved by lifting the guide 90 off drills 62, 64, 66, and removing drill 66 from the third hole 74. Then, a saw assembly (see 128 at FIG. 10, for example) is slid over drill 62 along axial bore 135 so that the practitioner can verify that the correct sized saw blade has been chosen. Preferably, the correct saw blade chosen will have a radius that forms a cut that leaves the tibial crest 28 intact and able to provide stability and support during the healing process. After verification, the saw assembly 128 is slid off the drill 62 and the guide 90 is slid onto the drill 62 only. Because of the bi-directionality of the guide 90, this may be either end aperture 96 or 98. Note in FIG. 9*a* that the orientation of guide 90 has been reversed so that the aperture 98 of end 94 is now adjacent the proximal end 14 of the tibia 10.

Figure 9A:
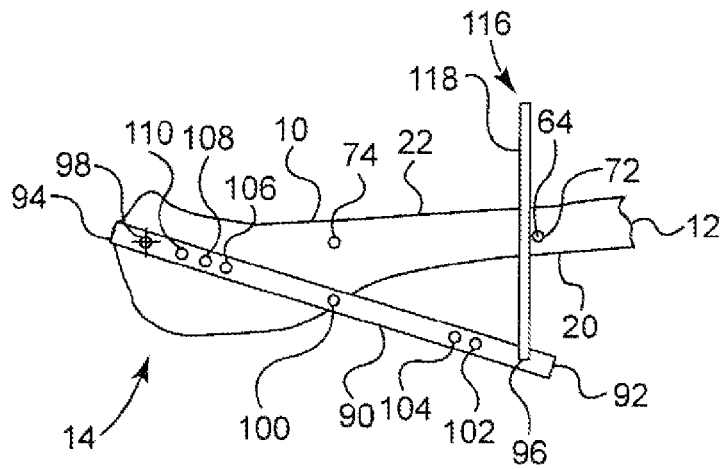
FIG. 9a is a plan view of an angle gauge used to position the guide for drilling a secondary hole in the proximal end of the tibia.
Figure 9B:
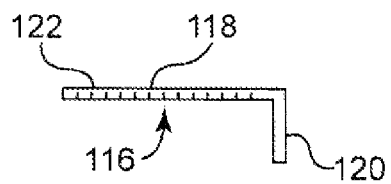

In order to facilitate location and drilling of the fourth hole 76, an angle gauge 116 is used. The gauge 116, as shown in FIGS. 9*a* and 9*b*, includes an elongated body 118 having a leg 120 that extends therefrom. In use, the leg 120 of the gauge is inserted into the most distal aperture of the guide 90 (shown in FIG. 9*b* as aperture 96. Note, however, if the guide 90 were reversed, this would be aperture 98) and the body 118 brought up against drill 64, which has been left in place in second hole 72. As will be appreciated, the body 118 of the angle gauge 116 may include indicia 120, which a practitioner may use to set the gauge angle. Using the gauge 116, the practitioner can quickly and accurately locate the location of the fourth hole 76 that will optimize placement of an optional fixation plate (see 200 in FIGS. 15-17, 19, and 20) so that the tibial plateau 38 will remain at about 5-6 degrees of slope.

As will be appreciated, the particular aperture of guide 90 used to drill the fourth hole 76 will depend upon the size of the particular saw blade used in the osteotomy procedure. Preferably, the fourth hole 76 will be adjacent the cut formed by the saw blade. Therefore, any one of the apertures 102, 104, 106, 108, or 110 may be used. Once the location for the fourth hole 76 has been chosen and located, it will be drilled using the guide 90.

Figure 15:
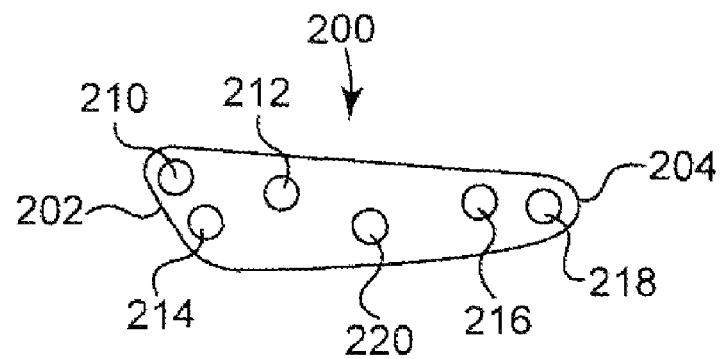
FIG. 15 is a plan view of a preferred embodiment of a fixation plate used to attach the tibial sections together.
Figure 16:
FIG. 16 is an edge view of the fixation plate of FIG. 15 in juxtaposition with a tibia.
Figure 17:
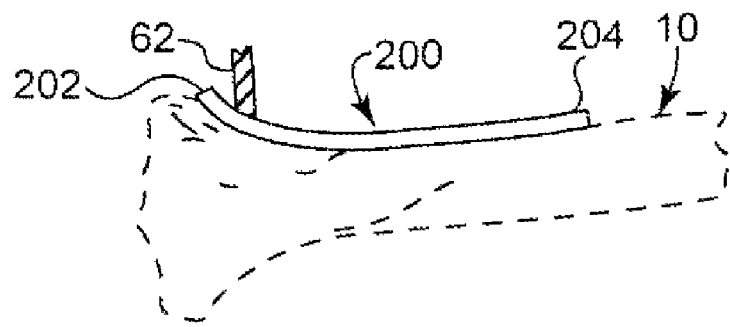
FIG. 17 is an edge view of the fixation plate of FIGS. 15 and 16 after it has been manipulated to fit the contours of a tibia.

After the fourth hole 76 has been drilled, the guide 90 is removed leaving the drill 62 in place in pilot hole 70. At this point, the optional fixation plate 200 may now be temporarily slid over the drill 62 so that it rests on the surface of tibia 10. As shown in FIG. 15, the fixation plate 200 has a first end 202, a second end 204, and a plurality of apertures 210, 212, 214, 216, and 220 that are arranged in a predetermined pattern. If the plate conforms to the contours of the bone to which it will ultimately be secured (see, FIG. 20), then no further action need be taken. If, however, the plate 200 does not conform to the contours of the bone, the plate may be removed and manipulated accordingly. Conformity of the plate 200 is then reassessed by sliding it over the drill 62 so that it again rests on the surface of the tibia 10. As will be understood, the process of fitting the fixation plate 200 to the surface of the tibia 10 may be repeated as necessary.

After the optional fixation plate 200 has been formed to fit the bone, it is slid off the drill 62 and the proximal end 14 of the tibia 10 is separated from the shaft by a saw assembly 128 as depicted in FIGS. 10 and 11. The saw assembly 128 includes mandrel 130 that has a shaft 132 having a splined end 134 and an axial bore 135. The mandrel also includes arms 136 and 138 that have notches 140 and 142, and apertures 144, 146, respectively. As can be seen, the notches 140 and 142 are sized to receive an adaptor 150, onto which a saw blade is removably attached. The adaptor 150 includes a flange 152 having tabs 154 and 156 that have apertures 158 and 160 that are configured and arranged to receive fastening elements 148. The adaptor 150 also includes a skirt 162 that has a predetermined thickness 164, and which is provided with apertures 166, 168, and 170 that correspond to apertures in a saw blade 174. As depicted in FIG. 11, the saw blade 174 includes an attachment end 176, a working end 178, and apertures 180, 182, and 184. The saw blade 174 is removably attached to the adaptor 150 by fastening elements 148 that extend through a collar 188 that has an inner surface 190, an outer surface 192 and apertures 194, 196, and 198.

Figure 13A:
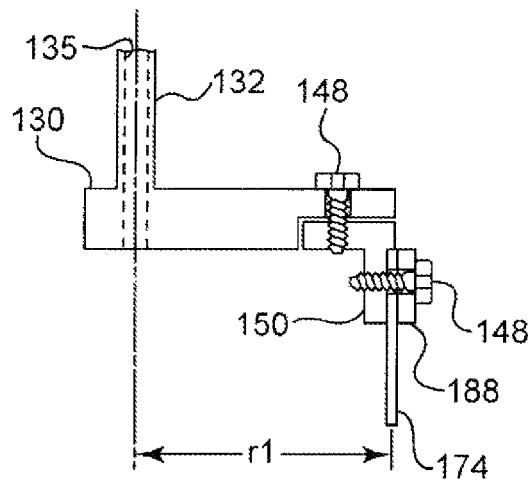
FIGS. 13a and 13b are partial side plan views of the saw assembly of FIGS. 10 and 11 in which a saw blade is removably attached at two locations on the assembly.
Figure 13B:
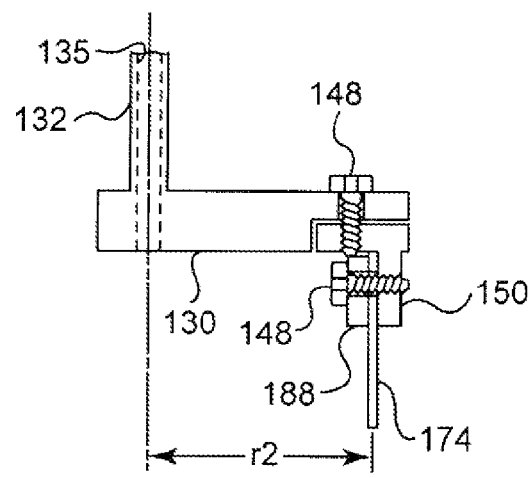

A feature of the saw assembly 128 is that the adaptor 150 is configured and arranged to retain a saw blade on either side of skirt 162. Thus, as shown in FIGS. 13*a* and 13*b*, the adaptor 150 is able to accommodate saw blades having different radii. So, for example, a saw blade having a radius of r1 would be attached to the outer surface of the skirt 162, while a saw blade having a radius of r2 would be attached to the inner surface of the skirt 162. Preferably, the skirt 162 has a thickness 164 of around 2.0 to 3.0 mm (see, FIG. 11).

The saw assembly 128 may include a second adaptor 151 that is shown in FIG. 12, and which is used to provide two additional mounting surfaces for two additional saw blades having different radii. Unlike the previously described adaptor 150 that has a distally located skirt, the second adaptor 151 has a proximally located skirt. The adaptor 151 includes a flange 153 having tabs 155 and 157 that have apertures 159 and 161 that are configured and arranged to receive fastening elements 148. The adaptor 151 also includes a skirt 163 that has a predetermined thickness 165, and which is provided with apertures 167, 169, and 171 that correspond to apertures in a saw blade.

Figure 14A:
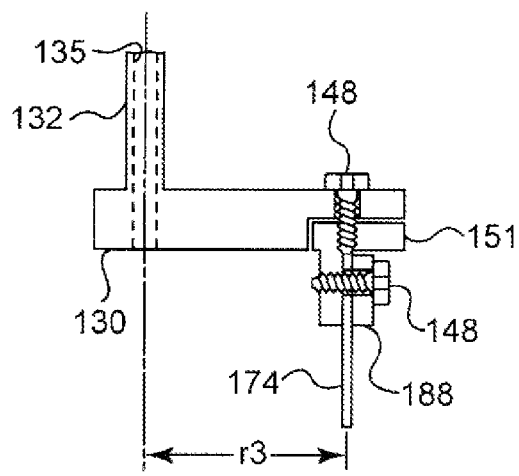
FIGS. 14a and 14b are partial side plan views of the saw assembly using the component of FIG. 12, and wherein a saw blade is removably attached at a second pair of locations on the assembly.
Figure 14B:
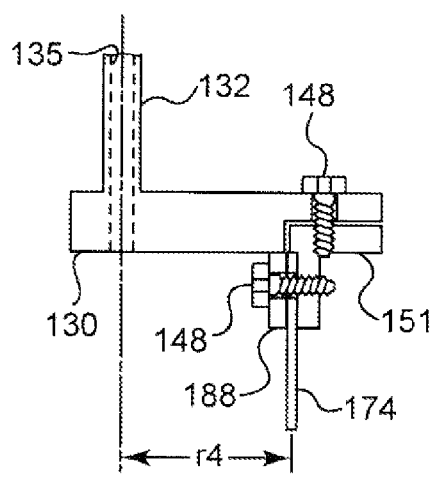

As with the first adaptor 150, the second adaptor 151 of the saw assembly 128 is configured and arranged to retain a saw blade on either side of the skirt 163. Thus, as shown in FIGS. 14*a* and 14*b*, the adaptor 151 is able to accommodate saw blades having different radii. So, for example, a saw blade having a radius of r3 would be attached to the outer surface of the skirt 163, while a saw blade having a radius of r4 would be attached to the inner surface of the skirt 163. Preferably, the skirt 163 has a thickness 165 of around 2.0 to 3.0 mm (see, FIG. 12).

Figure 18:
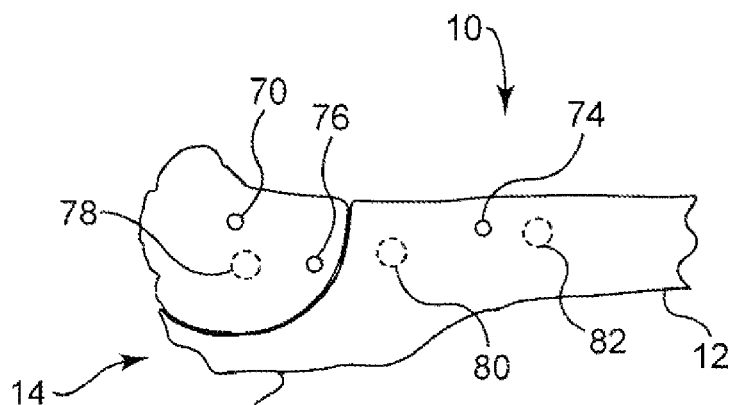
FIG. 18 is a partial, lateral side view of the upper or proximal end of the tibia of FIG. 1 after modification by the saw assembly.
Figure 19:
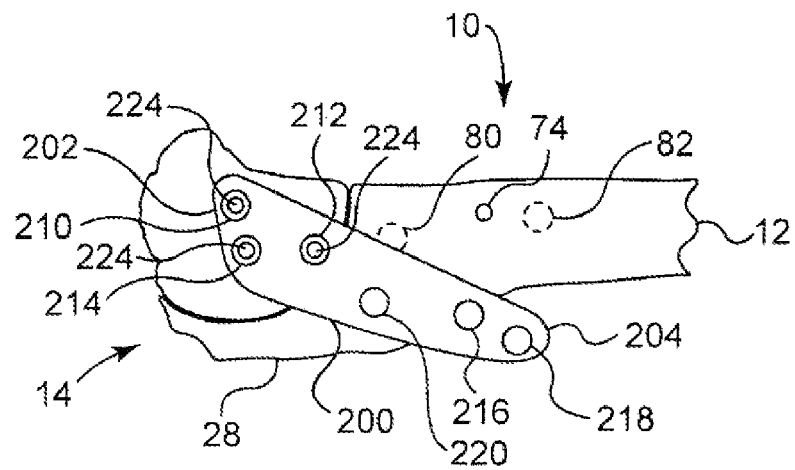
FIG. 19 is the tibia of FIG. 18 after the proximal end of the tibia has been attached to a fixation plate.
Figure 20:
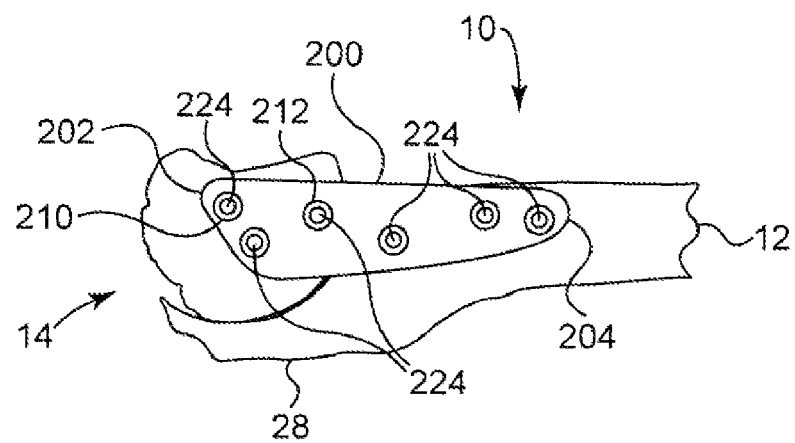
FIG. 20 is the tibia of FIG. 19 after the proximal end of the tibia has been rotated and the fixation plate has been attached to the tibia body.

After the saw assembly has been used and the proximal end 14 of the tibia 10 has been freed from the tibial shaft, the proximal end 14 will have the pilot hole 70 and, the fourth hole 76, while the shaft will have the third hole 74 and the second hole 72 (note that the second hole 72 is omitted from FIG. 18). At this point, the fixation plate 200 may now be attached to the proximal end 14 of the tibia 10 by using appropriately configured fastening elements 224 that extend through the apertures 210 and 212 of the plate 200 and into the existing holes 70 and 76 in the proximal end 14 of the tibia. This fixes the plate 200 to the proximal end 14 and provides the location for the third hole 78 (shown in dashed lines), which is then drilled and provided with a fastening element 224 as shown in FIG. 19. Next, the plate and the attached proximal end is rotated so that aperture 216 is brought into alignment with third hole 74 and affixed with a fastening element 224. This provides the location of the remaining two holes 80 and 82 (shown in dashed lines in FIGS. 18 and 19), which are then drilled and provided with fastening elements 224 as shown in FIG. 20. Note that during the final fitting of the fixation plate 200 to the tibia, the plate 200 may be further manipulated as necessary.

Figure 21:
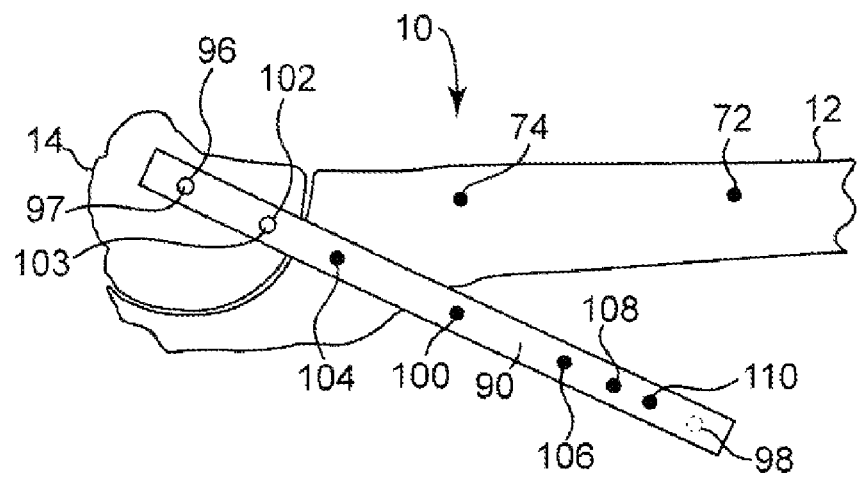
FIG. 21 is a partial, lateral side view of the upper or proximal end of the tibia of FIG. 1, after the proximal end of the tibia has been attached to a guide bar.
Figure 22:
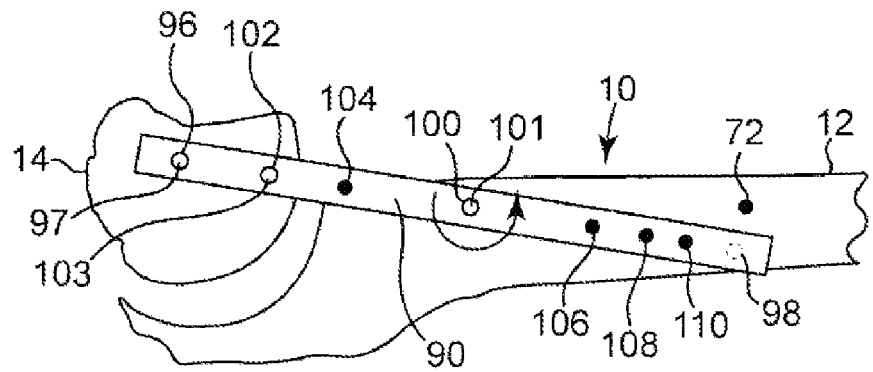
FIG. 22 is the tibia and guide bar of FIG. 21 after the guide bar after the guide bar has been pivotally attached to the shaft of the tibia; and, FIG. 23 is the tibia and guide bar of FIG. 22 after the guide bar with the proximal end of the tibia attached thereto has been rotated in a counter-clockwise direction about the pivot attachment on the shaft of the tibia.
Figure 23:
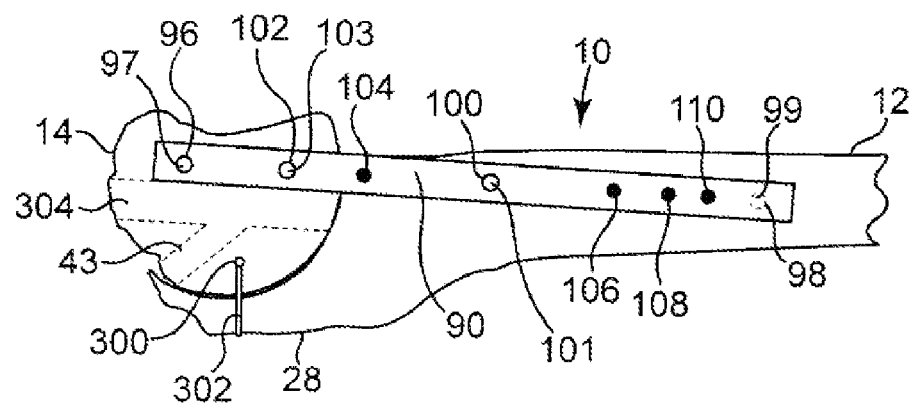

An alternative to the fixation plate method of attachment is depicted in FIGS. 21-23. In this method, all of the steps that are taken to form the pilot hole 70, the second hole 72, the third hole 74, the fourth hole 76, and the saw cut that separates the distal end 14 from the tibial shaft are the same as discussed above. However, with this alternative method of attachment the fixation plate is omitted. Instead, guide 90 is used. Starting with FIG. 21, the proximal end 14 of tibia 10, which has been freed from the tibial shaft, is attached to one end of the guide 90 at holes 96 and 102. This can be achieved using drill 62 (not shown) or a pin or dowel 97 that operatively connects hole 96 of guide 90 and pilot hole 70, and a pin or dowel 103 that operatively connects hole 102 of guide 90 and fourth hole 76. Another pin or dowel 101 is then used to operatively connect hole 100 of guide 90 to third hole 74 located in the tibial shaft. As shown in FIG. 22, pin or dowel 101 forms a pivot about which guide 90 may be rotated. As the guide 90 and the attached proximal end 14 are rotated (in this instance, counterclockwise), the proximal end 14 of the tibia is brought into contact with the remainder of the tibia, which minimizes the width of the kerf formed by the saw blade. After the proximal end 14 has been rotated into position, an aperture 300 is drilled in the proximal portion 14 and a cerclage wire 302 is used to further secure the pieces of the tibia together.

As will be understood, after the proximal end 14 of the tibia has been rotated into its new position, aperture 43 and the medullary canal of the tibial shaft will no longer be in alignment. Since access to the medullary canal is preferred in this alternative method of attachment, a new aperture 304 is drilled. After aperture 304 has been drilled, a suitable adhesive, preferably bone cement (not shown for purposes of clarity) is introduced into the aperture. After the bone cement is sufficiently hardened, the guide 90 is removed. The pins or dowels 97, 103, and 101 can be left in place and trimmed flush with the surface of the tibia.

In a variation of the aforementioned method of attachment, it will be understood that pin or dowel 101 may be omitted and that a pin or dowel 99 (shown in dashed line) may be used to operatively connect hole 98 of guide 90 to second hole 72 located in the tibial shaft. In this variation, the pin or dowel 99 would form the pivot point about which the guide 90 may be rotated. As with the previous method, after the proximal end has been rotated into position, an aperture may be drilled in the proximal portion and a cerclage wire used to further secure the pieces of the tibia together in a manner similar to FIG. 23. And similarly, it will be understood that a new aperture will be drilled into the proximal end to enable a suitable adhesive to be used to join the proximal end and the tibial shaft together. And, it will be further understood that the pins or dowels may be left in place and trimmed flush with the surface of the tibia.

In yet another variation of the aforementioned method of attachment, pins or dowels 101 and 99 may be used to operatively connect hole 100 of guide 90 to third hole 74, and hole 98 of guide 90 to second hole 72, respectively. With this variation, the step of attaching a cerclage wire may be omitted. The steps of introducing a suitable adhesive, removing the guide, and trimming the pins or dowels will remain the same.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

I claim:

1. A system for repairing anterior cruciate injuries in animals, the system comprising:
    a fixture used to locate and drill a pilot hole in a tibia, with the pilot hole generally transverse to a longitudinal axis of a tibia;
    a pin, the pin insertably receivable into the pilot hole such that a portion of the pin extends outwardly away from the tibia;
    a drill guide having plurality of apertures and a first portion that is rotatably connectable to the pin, the drill guide used to locate and drill additional generally transverse holes in the tibia;
    an angle gauge used to position the drill guide so that it is able to locate and drill the additional transverse holes in the tibia the angle gauge having a portion that is rotatably connectable to the pin; and
    a saw assembly for separating a portion of the proximal end of the tibia from the shaft of the tibia, so that the separated proximal end of the tibia can be repositioned and reattached to the shaft of the tibia, the saw assembly comprising a mandrel having a rotational axis, an adaptor connected to the mandrel, the adaptor having a surface that is spaced from and substantially parallel to the rotational axis of the mandrel, and a saw blade that is removably attachable to the surface of the adaptor, with the saw blade configured and arranged to form an arcuate cut in the proximal end of the tibia as the mandrel rotates about the rotational axis.

2. The system of claim 1, wherein the fixture comprises:
    a frame having an aperture that is configured to slidingly receive an intramedullary guide pin; and,
    an arm connectable to the frame and rotatably moveable with respect thereto, the arm having an aperture that is configured and arranged to receive and guide a drill used to form a pilot hole in a tibia.

3. The system of claim 1, wherein the drill guide comprises;
    an elongated body having a longitudinal axis, a first end and a second end, and a plurality of generally parallel apertures that extend transversely through the body and across the longitudinal axis.

4. The system of claim 1, wherein the angle gauge comprises an elongated body having indicia thereon and perpendicularly oriented leg configured and arranged to be inserted into an aperture in one end of the drill guide.

5. The system of claim 1, further comprising a fixation plate used to re-orient and secure the separated portion of the proximal end of the tibia to the shaft of the tibia.

6. The system of claim 5, wherein the fixation plate comprises a generally planar body having a plurality of transverse apertures arranged in a predetermined pattern and configured to receive fastening elements.

7. The system of claim 1, further comprising adhesive material for reattaching the separated portion of the proximal end of the tibia to the shaft of the tibia.

8. The system of claim 7, wherein the adhesive is bone cement.

9. The system of claim 1, wherein the saw assembly further comprises a set of multiple separate saw blades, each of which is removably connectable to the surface of the adaptor.

10. The system of claim 9, wherein each member of the set of saw blades has a substantially arcuate working end.

11. The system of claim 10, wherein the working end of each member of the set of saw blades has a different radii.

12. The system of claim 1, wherein the saw assembly further comprises a set of saw blades, with each saw blade removably connectable to the surface of the adaptor, with each of the members of the set of saw blades having a working end, and with at least two of the working ends configured to form pre-determined, differently shaped kerfs.

13. A system for repairing anterior cruciate injuries in animals, the system comprising:
    a fixture used to locate and drill a pilot hole in a tibia;
    a pin that is partially insertable into the pilot hole;
    a drill guide that is rotatably connectable to the pin, the drill guide used to locate and drill additional holes in the tibia;

an angle gauge that is rotatably connectable to the pin, the angle gauge used to position the drill guide so that it is able to locate and drill the additional holes in the tibia; and a saw assembly for separating a portion of the proximal end of the tibia from the shaft of the tibia so that it may be repositioned and reattached to the shaft, with the saw assembly comprising a mandrel having a rotational axis, a skirt connected to and positioned a predetermined distance from the rotational axis of the mandrel, and a set of saw blades, each of which is individually and removably connectable to the skirt of the saw assembly.

14. The system of claim 13, wherein the saw assembly rotates about the rotational axis, wherein the saw blade assembly moves in the direction of the rotational axis, and wherein one of the set of saw blades that is removably connected to the skirt separates the portion of the proximal end of the tibia from the shaft of the tibia.

15. The system of claim 13, wherein each member of the set of saw blades has a substantially arcuate working end.

16. The system of claim 13, wherein the fixture is used to locate and drill a pilot hole that is generally transverse to a longitudinal axis of a tibia.

17. The system of claim 13, wherein the drill guide includes a plurality of apertures and a first portion that is rotatably connectable to the pin.

18. The system of claim 17, wherein the angle gauge is connectable to a second portion of the drill guide, with the angle gauge used to position the drill guide so that it is able to locate and drill additional holes in a tibia.

* * * * *